United States Patent
Köhler et al.

(10) Patent No.: US 9,913,789 B2
(45) Date of Patent: Mar. 13, 2018

(54) FORMULATIONS CONTAINING SPHINGANINE

(71) Applicant: Evonik Degussa GmbH, Essen (DE)

(72) Inventors: Tim Köhler, Dorsten (DE); Mike Farwick, Essen (DE); Matthias Mentel, Dortmund (DE); Peter Lersch, Dinslaken (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/908,195

(22) PCT Filed: Jul. 1, 2014

(86) PCT No.: PCT/EP2014/063917
§ 371 (c)(1),
(2) Date: Jan. 28, 2016

(87) PCT Pub. No.: WO2015/014558
PCT Pub. Date: Feb. 5, 2015

(65) Prior Publication Data
US 2016/0184204 A1 Jun. 30, 2016

(30) Foreign Application Priority Data
Jul. 29, 2013 (DE) .................. 10 2013 214 713

(51) Int. Cl.
| | | |
|---|---|---|
| A61K 8/41 | (2006.01) |
| A61K 31/133 | (2006.01) |
| A61K 31/191 | (2006.01) |
| A61K 31/198 | (2006.01) |
| A61K 31/201 | (2006.01) |
| A61K 31/205 | (2006.01) |
| A61K 31/4168 | (2006.01) |
| A61K 31/4188 | (2006.01) |
| A61K 31/506 | (2006.01) |
| A61K 31/522 | (2006.01) |
| A61K 8/36 | (2006.01) |
| A61K 8/44 | (2006.01) |
| A61K 8/49 | (2006.01) |
| A61K 8/63 | (2006.01) |
| A61Q 5/12 | (2006.01) |
| A61Q 7/00 | (2006.01) |
| A61K 8/67 | (2006.01) |

(52) U.S. Cl.
CPC .............. *A61K 8/41* (2013.01); *A61K 8/361* (2013.01); *A61K 8/44* (2013.01); *A61K 8/4946* (2013.01); *A61K 8/4953* (2013.01); *A61K 8/63* (2013.01); *A61K 8/673* (2013.01); *A61K 31/133* (2013.01); *A61K 31/191* (2013.01); *A61K 31/198* (2013.01); *A61K 31/201* (2013.01); *A61K 31/205* (2013.01); *A61K 31/4168* (2013.01); *A61K 31/4188* (2013.01); *A61K 31/506* (2013.01); *A61K 31/522* (2013.01); *A61Q 5/12* (2013.01); *A61Q 7/00* (2013.01)

(58) Field of Classification Search
USPC .............. 514/263.34, 565; 424/59, 401
See application file for complete search history.

(56) References Cited

U.S. PATENT DOCUMENTS

| | | | | |
|---|---|---|---|---|
| 5,776,480 A | * | 7/1998 | Candau .................. | A61K 8/68 424/401 |
| 6,184,252 B1 | | 2/2001 | Fagot et al. | |
| 6,706,502 B2 | | 3/2004 | Gruning et al. | |
| 7,687,055 B2 | | 3/2010 | Bimczok et al. | |
| 8,318,676 B2 | | 11/2012 | Bimczok et al. | |
| 8,664,175 B2 | | 3/2014 | Wenk et al. | |
| 8,703,159 B2 | | 4/2014 | Wenk et al. | |
| 2004/0018162 A1 | | 1/2004 | Bimczok et al. | |
| 2004/0171693 A1 | | 9/2004 | Gan et al. | |
| 2007/0277332 A1 | | 12/2007 | Bimczok et al. | |
| 2009/0104294 A1 | * | 4/2009 | Wenk .................. | A61K 8/97 424/756 |
| 2012/0308503 A1 | | 12/2012 | Wenk et al. | |
| 2013/0071340 A1 | | 3/2013 | Wenk et al. | |
| 2014/0170092 A1 | | 6/2014 | Farwick et al. | |

FOREIGN PATENT DOCUMENTS

| | | |
|---|---|---|
| CA | 2 678 135 | 9/2004 |
| CH | 399 655 | 9/1965 |
| DE | 203 15 174 | 12/2003 |
| DE | 20 2005 011 009 | 12/2005 |
| EP | 2 140 857 | 1/2010 |
| FR | 2 820 037 | 8/2002 |
| WO | WO 2012/084876 | 6/2012 |

OTHER PUBLICATIONS

English translation of the International Search Report for corresponding international application PCT/EP2014/063917 filed Jul. 1, 2014.
English language translation of the Written Opinion of the International Searching Authority for corresponding application PCT/EP2014/063917 filed Jul. 1, 2014.
English language translation of the International Preliminary Report on Patentability for corresponding international application PCT/EP2014/063917 filed Jul. 1, 2014.
Fischer, et al., "Effect of caffeine and testosterone on the proliferation of human hair follicles in vitro," *International Journal of Dermatology* 46(1):27-35 ((Jan. 2007).
Foitzik, et al., "Indications that topical L -carnitin-L -tartrate promotes human hair growth in vivo," *Journal of Dermatological Science* 48(2):141-144 (Nov. 2007).
Herman, et al., "Caffeine's Mechanisms of Action and Its Cosmetic Use," *Skin Pharmacol. Physiol.* 26(1):8-14 (published online Oct. 2012).
Rossi, et al., "Minoxidil Use in Dermatology, Side Effects and Recent Patents," *Recent Patents on Inflammation & Allergy Drug Discovery* 6(2):130-136 (accepted Feb. 2012).

* cited by examiner

*Primary Examiner* — Pancham Bakshi
(74) *Attorney, Agent, or Firm* — Law Office of: Michael A. Sanzo, LLC

(57) ABSTRACT

The present invention relates to formulations comprising
A) sphinganine and
B) at least one active ingredient selected from the group creatine, creatinine, caffeine, carnitine, biotin, arjunolic acid, xymenynic acid, minoxidil, arginine and derivatives thereof.

16 Claims, 2 Drawing Sheets

Figure 1:
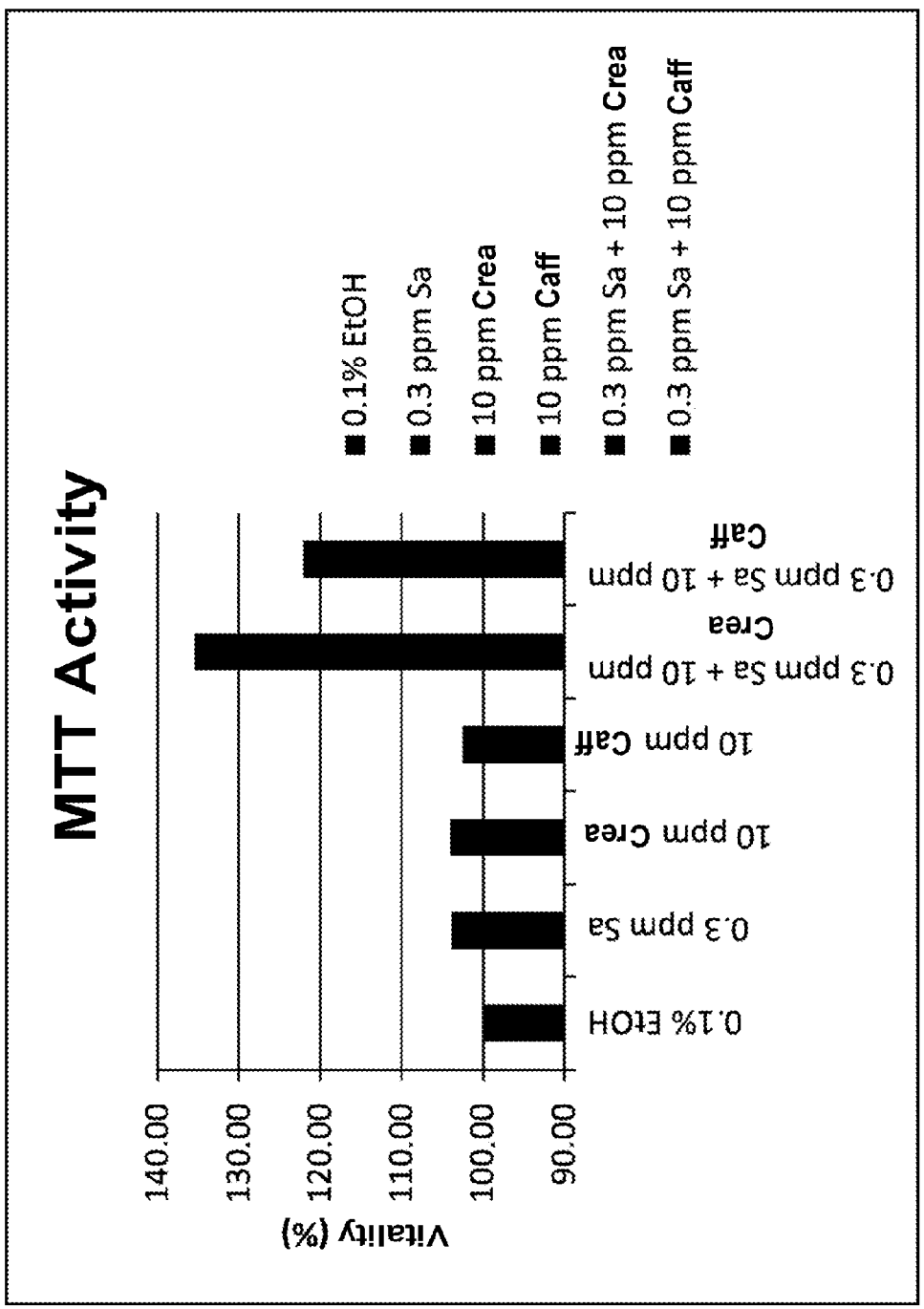

| Spreadability very difficult | 0 | 1 | 2 | 3 | 4 | 5 | 6 | 7 | 8 | 9 | 10 | very easy |
|---|---|---|---|---|---|---|---|---|---|---|---|---|
| Absorption no absorption | 0 | 1 | 2 | 3 | 4 | 5 | 6 | 7 | 8 | 9 | 10 | considerable absorption |
| Oiliness not oily | 0 | 1 | 2 | 3 | 4 | 5 | 6 | 7 | 8 | 9 | 10 | very oily |
| Waxiness not waxy | 0 | 1 | 2 | 3 | 4 | 5 | 6 | 7 | 8 | 9 | 10 | very waxy |
| Slippiness not slippy | 0 | 1 | 2 | 3 | 4 | 5 | 6 | 7 | 8 | 9 | 10 | very slippy |
| Stickiness not sticky | 0 | 1 | 2 | 3 | 4 | 5 | 6 | 7 | 8 | 9 | 10 | very sticky |
| Silkiness/velvetiness not velvety/silky | 0 | 1 | 2 | 3 | 4 | 5 | 6 | 7 | 8 | 9 | 10 | very velvety/silky |

Figure 2

FORMULATIONS CONTAINING SPHINGANINE

CROSS REFERENCE TO RELATED APPLICATIONS

The present application is US national stage of international application PCT/EP2014/063917, which had an international filing date of Jul. 1, 2014, and which was published in German under PCT Article 21(2) on Feb. 5, 2015. Priority is claimed to German application DE 102013214713.9, filed on Jul. 29, 2013.

FIELD OF THE INVENTION

The present invention relates to formulations comprising
A) sphinganine and
B) at least one active ingredient selected from the group creatine, creatinine, caffeine, carnitine, biotin, arjunolic acid, xymenynic acid, minoxidil, arginine and derivatives thereof.

PRIOR ART

Large sections of the human population suffer from hair loss or slowed hair growth, particularly during advancing years. In the extreme case, this manifests itself by partial or complete baldness.

The human hair is subject to a complex growth cycle which can be divided into three characteristic phases: An anagen phase lasting several years in which the hair grows, a short catagen phase (transition phase) lasting several weeks, and a telogen phase (resting phase) which lasts several months. If one cycle is complete, a new cycle generally follows in order to replace the hair that has fallen out. This process lasts a lifetime for undisturbed hair growth, but can be disturbed. Corresponding to the complex hair growth cycle, the causes of hair loss are manifold and in some cases gender-specific.

Often, the growth phases of the hair shorten with increasing age, leading to the formation of shorter and/or finer hair (vellus hair). Shifting the ratio of actively growing hair to hair in the resting phase (anagen:telogen ratio) can lead to reduced hair density. In the extreme case, the hair growth cycle comes to a stop completely, which then results in the phenomenon of baldness.

Men are more often affected by hair loss compared to women. In contrast to women, they often suffer from a gender-specific form of hair loss, so-called androgenetic or androgenic alopecia. This form of hair loss is hereditary and often arises at a young age. The main cause of this form of hair loss in the steroid hormone dihydrotestosterone (DHT). It is formed in the human body by the enzyme steroid-5-alpha-reductase from the male sex hormone testosterone and, in the event of inherited DHT hypersensitivity, leads to the shortening of the anagen phase of the hair. Another form of hair loss, so-called alopecia areata, refers to locally limited, circular hair loss. This form of hair loss is an inflammatory autoimmune disease and can occur at any age.

One form of hair loss which is primarily observed in women is diffuse alopecia. This results in a time-limited loss of hair, the possible causes being diverse, e.g. hormone fluctuations, stress or lack of iron.

In the cosmetic or pharmaceutical industry, a number of compounds have been described in order to reduce the visible effects of alopecia. Some of the proposed substances can prevent the loss of hair or at least reduce this. Other substances can stimulate the growth of hair, particularly by stimulating the hair follicles for growth and as a result a new hair growth cycle is initiated.

The described pharmaceutical active ingredients that are used successfully for treating alopecia include inter alia steroid hormones such as e.g. finasteride or dutasteride, alfatradiol or 17α-estradiol, as well as cortisone-containing preparations. Although positive effects have been demonstrated for these substances, undesired side effects often arise since they are pharmacologically active substances. Furthermore, the specified substances are often specifically effective only for men, but cannot be used universally. The positive effects are also in most cases inadequate, i.e. the alopecia is only partially prevented or reduced. Moreover, the positive effects are in most cases only temporary, i.e. following continued application or if the preparation is stopped the starting state is restored. Alongside the pharmacologically effective substances, a series of cosmetic active ingredients has also been proposed for treating hair loss/promoting hair growth. These include various vitamins (in particular vitamins of the B series, e.g. vitamin B7 or biotin), amino acids (in particular L-valine, L-arginine) and amino acid derivatives (e.g. creatine, L-carnitine), which, inter alia, stimulate the cell metabolism. And also caffeine which, primarily by stimulating the microcirculation, stimulates blood flow through the scalp and indirectly hair growth. Furthermore, a series of plant extracts has been described for stimulating hair growth, including extracts of saw palmetto.

Besides the substances already discussed above, a large number of molecules and complex mixtures have been described in the context of stimulating hair growth. These include the following plant extracts or pure substances, as well as derivatives derived therefrom or precursors:

acetyltyrosine, allantoin, bioquinone (Ubiquinon, Coenzyme Q10), amino acids (primarily arginine, serine, methionine), *Arctium Majus* root extract, biotinoyl tripeptide-1, bisabolol, *Boswellia serrata* extract (incense), L-carnitine, L-carnitine L-tartrate, acetyl carnitine, palmitoyl carnitine, *Carthamus tinctorius* glucosides, diethyl lutidinate (diethyl 2,4-pyridinedicarboxylate; stemoxydine), *Echinacea* extracts, ectoin, *Emblica officianalis* (*Phyllantus emblica*) extract, epigallocatechin gallate (EGCG), estron, fluridil (Eucapil), *Ginkgo Biloba* extract, glabranin, glycyrrhic acid, *Kigelia africana* extract, kopexil (Aminexil; 2,3-dihydro-3-hydroxy-2-imino-4-pyrimidineamine), *Lithothamnion Calcareum* extract, minerals (in particular magnesium, calcium and zinc salts), minoxidil, *Moringa* plant extracts, nicotinic acid (vitamin B3, niacin), nicotinamide (niacinamide), oxaloacetate, *Panax Ginseng* root extract, panthenol, pantothenic acid (vitamin B5), pantolactone, *Paullinia Cupana* extract (Guarana), plant protein hydrolysates, progesterone, saw palmetto berry extract (Serenoa), salicylic acid, *Salvia Officinalis* extract, *Sargassum Filipendula* extract, *Sophora* root extract, taurine (2-aminoethanesulphonic acid), tocopherol (vitamin E), *Tropaeolum Majus* extract, xanthines (including theophylline, theobromine), *Zingiber Officinale* root extract, ergothionene, lycopine, marine glycogen, gluconate salts, Indian cress, synthetic thymus hydrolysate, trichogen, tea tree oil, burdock extract, gingko biloba leaf extract, algae extracts, green tea extract.

However, still none of the aforementioned substances has hitherto exhibited long-lasting satisfactory results for stimulating hair growth, meaning that the need to develop newtypes of cosmetic active ingredients for more efficient stimulation of hair growth and/or reducing hair loss is unbroken. Preference is given here to natural, endogenous compounds.

EP0790053 describes the use of a 2-aminoalkane-1,3-diol for slowing hair loss and/or for triggering and stimulating hair growth. Here, it was shown that the treatment of ex vivo hair follicles kept in culture with sphinganine increases the lifespan of the hair follicles. Furthermore, a growth-promoting effect of sphinganine on in vitro cultivated keratinocytes was demonstrated.

DE102011109546 describes the use of sphinganine for improving the visual appearance of skin and hair.

CA2678135 discloses a method for stimulating the growth of hair follicles by applying a formulation comprising creatine. The method can be used to prevent male androgenetic hair loss, age-related hair loss or hair loss triggered by chemotherapy or exposure to drugs.

Further evidence of stimulating effects of creatine on hair growth can be found by way of example in US20040171693, EP2140857 and WO2012084876.

Positive effects of caffeine on the growth of hair are generally known. The prior art is described inter alia in the following documents: Herman A, Herman A P; Skin Pharmacology and Physiology, Vol. 26 (1), 8-14, 2013. Fischer, T W, Hipler, U C, Elsner, P; International Journal of Dermatology Vol. 46 (1), 27-35, 2007. Further examples can be found in DE202005011009 and WO2012084876.

Promoting effects of L-carnitine or L-carnitine derivatives are described in the following documents: Foitzik, K, Hoting, E, Heinrich, U, Tronnier, H, Paus, R; Journal of Dermatological Science 48 (2), 141-144, 2007. DE202005011009.

The use of biotin, e.g. for stimulating hair growth or for improving the structure of the hair is widespread. An overview can be found by way of example in the following review: Noser, F, Bimczok, R; SOFW Journal 122 (8), 511-515, 1996.

The topical application of minoxidil for stimulating hair growth is also widespread. The prior art is described by way of example in the following review: Rossi, A, Cantisani, C, Melis, L, Iorio, A, Scali, E, Calvieri, S; Recent Patents on Inflammation & Allergy Drug Discovery 6 (2), 130-136, 2012.

Similarly, the use of arginine for stimulating hair growth is known. One example of this can be found in DE20315174.

It was an object of the invention to provide formulations which stimulate hair growth and have outstanding sensory properties.

DESCRIPTION OF THE INVENTION

Surprisingly, it has been found that the active ingredient combinations described below are able to solve the problem addressed by the invention.

The present invention therefore provides formulations, in particular cosmetic and pharmaceutical formulations, comprising
A) sphinganine and
B) at least one active ingredient selected from the group creatine, creatinine, caffeine, carnitine, biotin, arjunolic acid, xymenynic acid, minoxidil, arginine and derivatives thereof.

The invention further provides component A) and B) for stimulating hair growth on the scalp.

It is an advantage of the invention that the formulations have superior sensory properties which lead to an improved skin feel and/or hair feel.

A further advantage of the present invention is that the formulations stimulate in vitro human follicular dermal papilla cells (HFDPCs) to proliferate, which in vivo equates to stimulation of hair growth. Surprisingly, the combination of sphinganine with in each case one of the additional active ingredients has proven here to be significantly more effective compared to the sum of the inductions of cell proliferation which could be achieved by means of the respective individual substances.

It is a further advantage of the present invention that the formulations have improved distributability compared to the individual components.

It is a further advantage of the present invention that the formulations have an improved absorption compared to the individual components.

It is a further advantage of the present invention that the formulations have reduced oiliness compared to the individual components.

It is a further advantage of the present invention that the formulations have reduced waxiness compared to the individual components.

It is a further advantage of the present invention that the formulations have improved slippiness compared to the individual components.

It is a further advantage of the present invention that the formulations have reduced stickiness compared to the individual components.

It is a further advantage of the present invention that the formulations have improved silkiness/velvetiness compared to the individual components.

The term "derivative" is preferably understood as meaning acids, esters, amides, alcohols, alcoholates, aldehydes, amines, salts, hydrates, glucosides, isomers and enantiomers of the specified starting compound.

Unless stated otherwise, all of the stated percentages (%) are percent by mass.

Preferred formulations according to the invention comprise, as component B), derivatives of creatine, creatinine, caffeine, carnitine, biotin, arjunolic acid, xymenynic acid, minoxidil and arginine selected from the group creatine hydrates, disodium phosphocreatine, caffeine benzide, caffeine carboxylic acid, caffeine hydrates, carnitine HCl, acetyl carnitine, acetyl carnitine HCl, carnitine fumarate, carnitine hydroxycitrate, carnitine linoleate, carnitine pyroglutamate, carnitine tartrate, palmitoyl carnitine, D/L-carnitine, D/L-carnitine HCl, hexadecanoyl carnitine, levo carnitine, allantoin biotin, biotinoyl hexapeptide-2 amide, biotinoyl pentapeptide-4, biotinoyl tripeptide-1, biotinoyl tripeptide-35, ethyl biotinate, monoethanolamine biotinate, biotin ethyl ester, biotinum, acetyl arginine and arginine HCl.

Xymenynic acid is used as component B) in formulations according to the invention preferably in the form of an extract from the sandlewood tree, for example as santalum album extract.

Arjunolic acid is used as component B) in formulations according to the invention preferably in the form of an extract from the bark or the wood of the terminalia arjuna tree. Consequently, in this case, the formulation according to the invention comprises, in addition to the arjunolic acid, preferably asiatic acid and/or its glucoside, in particular in a weight ratio of 10:1 to 2:1.

In a preferred embodiment of the formulation according to the invention, component B) is selected from creatine, creatinine, caffeine and derivatives thereof since component A) and B) synergistically complement one another in their effect relating to hair growth.

Preferably, the following formulations are excluded from those according to the invention:

| | |
|---|---|
| Laureth-4 | 0.5% |
| PEG-40 Hydrogenated Castor Oil | 0.5% |
| Sphinganine | 0.1% |
| Quaternium-80 | 0.4% |
| Dimethicone Propyl PG-Betaine | 0.6% |
| Cetrimonium Chloride | 0.8% |
| Water | ad 100.0% |
| Creatine | 0.5% |
| Ethanol | 15.0% |
| PVP/VA Copolymer | 4.0% |
| Sodium Hydroxide (10% in water) | 1.2% |

| | | | | |
|---|---|---|---|---|
| Decyl Oleate | 5.7% | 5.7% | 5.7% | 5.7% |
| Ethylhexyl Stearate | 7.3% | 7.3% | 7.3% | 7.3% |
| Glyceryl Stearate | 0.5% | 0.5% | 0.5% | 0.5% |
| Stearic Acid | 0.7% | 0.7% | 0.7% | 0.7% |
| Ceteareth-25; glycerin; cetyl alcohol; behenic acid; cholesterol; ceramide EOP; ceramide EOS; ceramide NP; ceramide NS; ceramide AP; caproyl-phytosphingosine; caproyl-sphingosine. | — | 0.5% | — | 0.5% |
| Salicyloyl Phytosphingosine | — | — | 0.05% | 0.03% |
| Creatine | 0.5% | 0.2% | 0.1% | 0.2% |
| Cetearyl Glucoside | 1.0% | 1.0% | 1.0% | 1.0% |
| Glycerin | 3.0% | 3.0% | 3.0% | 3.0% |
| Carbomer | 0.2% | 0.2% | 0.2% | 0.2% |
| Sodium Hydroxide (10%) | 0.7% | 0.7% | 0.7% | 0.7% |
| Ethanol | 9.5% | 5.7% | 3.8% | 7.6% |
| Sphinganine | 0.33% | 0.20% | 0.13% | 0.26% |
| Water | ad 100.0% | ad 100.0% | ad 100.0% | ad 100.0% |

| | | |
|---|---|---|
| Cetyl PEG/PPG-10/1 Dimethicone | 2.0% | 2.0% |
| Microcrystalline Wax | 0.5% | 0.5% |
| Hydrogenated Castor Oil | 0.5% | 0.5% |
| Decyl Oleate | 9.0% | 9.0% |
| Caprylic/Capric Triglyceride | 10.0% | 10.0% |
| Diethylhexyl Carbonate | 5.0% | 5.0% |
| PPG-3 Myristyl Ether; Salicyloyl Phytosphingosine | 3.0% | 3.0% |
| Sodium Chloride | 0.5% | 0.5% |
| Creatine | 0.2% | 0.1% |
| Betaine | — | 0.3% |
| Urea | — | 0.1% |
| Ethanol | 1.9% | 2.85% |
| Sphinganine | 0.07% | 0.1% |
| Water | ad 100.0% | ad 100.0% |

| | |
|---|---|
| Disodium PEG-5 Lauryl citrate Sulfosuccinate; Sodium Laureth Sulphate | 8.0% |
| Sodium Cocoamphoacetate | 12.0% |
| Capryl/Capramidopropyl Betaine | 2.0% |
| Polyglyceryl-3 Caprate | 0.3% |
| PPG-3 Myristyl Ether | 0.5% |
| Sphinganine | 0.1% |
| Water | 77.2% |
| D-Panthenol | 0.2% |
| Creatine | 0.5% |
| Methoxy PEG/PPG-7/3 Aminopropyl Dimethicone | 0.2% |

Formulations according to the invention comprise component A) preferably in a concentration of from 0.01% by weight to 5.0% by weight, preferably from 0.05% by weight to 1.0% by weight, particularly preferably from 0.1% by weight to 0.5% by weight, the percentages by weight referring to the total formulation.

Formulations according to the invention comprise component B) preferably in a concentration of from 0.01% by weight to 20% by weight, preferably from 0.1% by weight to 10.0% by weight, particularly preferably from 1.0% by weight to 5.0% by weight, the percentages by weight referring to the total formulation.

The weight ratio of component A) to component B) in the formulation according to the invention is preferably 1:1 to 1:2000, preferably from 1:2 to 1:200, particularly preferably from 1:10 to 1:50.

The formulations according to the invention can comprise e.g. at least one further additional component selected from the group of emollients, coemulsifiers, thickeners/viscosity regulators/stabilizers, antioxidants, hydrotropes (or polyols), solids and fillers, pearlescence additives, deodorant and antiperspirant active ingredients, insect repellents, self-tanning agents, preservatives, conditioners, perfumes, dyes, cosmetic active ingredients, care additives, superfatting agents, solvents.

Substances which can be used as exemplary representatives of the individual groups are known to the person skilled in the art and can be found for example in the German application DE 102008001788.4. This patent application is herewith incorporated as reference and thus forms part of the disclosure.

As regards further optional components and the amounts of these components used, reference is made expressly to the relevant handbooks known to the person skilled in the art, e.g. K. Schrader, "Grundlagen and Rezepturen der Kosmetika [Fundamentals and Formulations of Cosmetics]", 2nd edition, pages 329 to 341, Hüthig Buch Verlag Heidelberg.

The amounts of the particular additives are governed by the intended use.

Typical guide formulations for the respective applications are known prior art and are contained for example in the brochures of the manufacturers of the particular basic materials and active ingredients. These existing formulations can usually be adopted unchanged. If necessary, the desired modifications can, however, be undertaken without complication by means of simple experiments for the purposes of adaptation and optimization.

Since the formulations according to the invention promote hair growth to an unexpected degree, the invention further provides a composition comprising A) sphinganine and B) at least one active ingredient selected from the group creatine, creatinine, caffeine, carnitine, biotin, arjunolic acid, xymenynic acid, minoxidil, arginine and derivatives thereof for stimulating hair growth, in particular on the scalp, preferably that of a human being.

Similarly, the compositions according to the invention generally prevent hair loss, and the invention therefore further provides a composition comprising A) sphinganine and B) at least one active ingredient selected from the group creatine, creatinine, caffeine, carnitine, biotin, arjunolic acid, xymenynic acid, minoxidil, arginine and derivatives thereof for treating hair loss.

The compositions according to the invention correspond in their preferred embodiments to the preferred embodiments of the formulations according to the invention.

Additionally, it has been found that the specific combinations of the active ingredients also exert a promoting effect on the structure of the hair, as a result of which its stability, resistance, colour intensity and loadability is increased. Consequently, the invention further provides the use of a composition comprising A) sphinganine and B) at least one active ingredient selected from the group creatine, creatinine, caffeine, carnitine, biotin, arjunolic acid, xymenynic acid, minoxidil, arginine and derivatives thereof for hair conditioning.

The use according to the invention is a cosmetic use in which preferably component A) and B) are used according to the preferred embodiments of the formulations according to the invention.

The examples listed below illustrate the present invention by way of example, without any intention of restricting the invention, the scope of application of which is apparent from the entirety of the description and the claims, to the embodiments specified in the examples.

The following figures are a component of the examples:

FIG. 1: Synergistic induction of cell proliferation by sphinganine in combination with creatine or caffeine. EtOH, ethanol; Sa, sphinganine; Crea, creatine; Caff, caffeine.

FIG. 2: Sensory panel assessment scale

EXAMPLES

Example 1: Stimulation of the Proliferation of Human Follicular Dermal Papilla Cells (HFDPCs) by Sphinganine in Combination with Caffeine or Creatine HFDPCs, media and other chemicals for the cell cultivation experiments were acquired from Promocell (Heidelberg, Germany). The cells were sown in a cell density of about 6300 cells/cm$^2$ in a T75 bottle with follicle dermal papilla cell growth medium (for short: growth medium) and then incubated at 37° C., 5% $CO_2$. After 1 day, media exchange was carried out. After a further 3 days, the medium was removed, the cells were washed with PBS (phosphate buffered saline) (without $Mg^{2+}$ and $Ca^{2+}$), detached by accutase treatment; the cell count is determined and then the cells are sown in a concentration of about 5500 cells/cm$^2$ in new T75 bottles in growth medium and further cultivated under identical conditions as described above. After 1 and 3 days, media exchange was carried out. After 1 further day, the medium was removed, the cells were washed in PBS (without $Mg^{2+}$ and $Ca^{2+}$), detached by accutase treatment and then sown in a concentration of about 10 000 cells/cm$^2$ into the cavities of 6-well cell culture plates with 2.5 ml of growth medium in each case. After 1 day, media exchange was carried out, and the test substances—diluted in fresh medium—were applied. The following concentrations of the test substances were used: sphinganine 0.3 µg/ml; creatine 10 µg/ml; caffeine 10 µg/ml. All cultivations were carried out in the presence of 0.1% (v/v) ethanol and a corresponding vehicle control was performed at the same time. After incubation for 24 hours, an MTT assay was carried out. The activity in the MTT test indicates the activity of the mitochondrial dehydrogenase and is a marker for the cell vitality and the proliferation capacity. Firstly, a 10 mg/ml stock solution of the MTT reagent (Thiazolyl Blue Tetrazolium Bromide, Sigma Aldrich M5655) in PBS was prepared. The stock solution was then diluted with growth medium to an end concentration of 1 mg/ml MTT reagent. The cells were washed with PBS (without $Mg^{2+}$ and $Ca^{2+}$) and incubated with 1 ml of growth medium with MTT reagent for 3 h at 37° C. The medium was then completely removed and, to extract the blue formazane dye formed, in each case 1 ml of isopropanol was added per well. Incubation was then carried out for 1 h at room temperature on a vertical shaker. Afterwards, 200 µl of the isopropanol extract from each well were transferred to a well of a 96-well microtiter plate. The absorption of the extracts was determined by spectrophotometry at a wavelength of 550 nm. The optical density of the extracts from the cells treated only with the vehicle is regarded as the reference (100%), all of the other measured values are quantified relative to the reference sample. The results are shown in FIG. 1. Sphinganine (103.9%), creatine (104.0%) and caffeine (102.5%) on their own show moderate stimulation of cell proliferation compared to the vehicle control. Surprisingly, a considerably more marked positive effect on the cell proliferation is achieved by the combination of sphinganine with creatine (135.5%) or with caffeine (122.1%).

Example 2: Improved Sensory Properties of Cosmetic Formulations Comprising Sphinganine in Combination with Further Cosmetic Active Ingredients Cosmetic cream formulations comprising at least one cosmetic active ingredient selected from the group of sphinganine, creatine, creatinine, caffeine, carnitine, biotin, arjunolic acid, xymenynic acid, minoxidil and arginine were used in a panel test in order to evaluate the sensory properties of the applied cream formulations. The composition of the cream formulations is shown in Table 1.

Customary formulation processes known to the person skilled in the art were used to produce the formulations.

TABLE 1

Cream formulations used (data in percent by mass)

| Raw material | A | B | C | D | E | F | G | H | I | J | K |
|---|---|---|---|---|---|---|---|---|---|---|---|
| TEGIN ® 4100 (Glyceryl Stearate) | 2.0 | 2.0 | 2.0 | 2.0 | 2.0 | 2.0 | 2.0 | 2.0 | 2.0 | 2.0 | 2.0 |
| TEGO ® Alkanol 1618 (Cetearyl Alcohol) | 3.0 | 3.0 | 3.0 | 3.0 | 3.0 | 3.0 | 3.0 | 3.0 | 3.0 | 3.0 | 3.0 |
| Stearic Acid | 1.0 | 1.0 | 1.0 | 1.0 | 1.0 | 1.0 | 1.0 | 1.0 | 1.0 | 1.0 | 1.0 |
| TEGOSOFT ® AC (Isoamyl Cocoate) | 2.0 | 2.0 | 2.0 | 2.0 | 2.0 | 2.0 | 2.0 | 2.0 | 2.0 | 2.0 | 2.0 |
| TEGOSOFT ® M (Isopropyl Myristate) | 4.5 | 4.5 | 4.5 | 4.5 | 4.5 | 4.5 | 4.5 | 4.5 | 4.5 | 4.5 | 4.5 |
| TEGOSOFT ® CT (Caprylic/Capric Triglyceride) | 7.3 | 7.3 | 7.3 | 7.3 | 7.3 | 7.3 | 7.3 | 7.3 | 7.3 | 7.3 | 7.3 |
| TEGO ® Care CG 90 (Cetearyl Glucoside) | 1.0 | 1.0 | 1.0 | 1.0 | 1.0 | 1.0 | 1.0 | 1.0 | 1.0 | 1.0 | 1.0 |
| TEGO ® Carbomer 134 (Carbomer) | 0.2 | 0.2 | 0.2 | 0.2 | 0.2 | 0.2 | 0.2 | 0.2 | 0.2 | 0.2 | 0.2 |
| Glycerin | 3.0 | 3.0 | 3.0 | 3.0 | 3.0 | 3.0 | 3.0 | 3.0 | 3.0 | 3.0 | 3.0 |
| Sodium Hydroxide (10%) | 0.4 | 0.4 | 0.4 | 0.4 | 0.4 | 0.4 | 0.4 | 0.4 | 0.4 | 0.4 | 0.4 |
| Sphinganine | | 0.2 | | | | | | | | | |
| Creatine | | | 1.0 | | | | | | | | |
| Caffeine | | | | 1.0 | | | | | | | |
| Carnitine | | | | | 0.5 | | | | | | |
| Biotin | | | | | | 0.5 | | | | | |
| Arjunolic acid | | | | | | | 0.2 | | | | |
| Xymenynic acid | | | | | | | | 0.2 | | | |
| Minoxidil | | | | | | | | | 1.0 | | |
| Arginine | | | | | | | | | | 1.0 | |
| Creatinine | | | | | | | | | | | 1.0 |
| Water | 75.6 | 75.4 | 74.6 | 74.6 | 75.1 | 75.1 | 75.4 | 75.4 | 74.6 | 74.6 | 74.6 |

| Raw material | B + C | B + D | B + E | B + F | B + G | B + H | B + I | B + J | B + K |
|---|---|---|---|---|---|---|---|---|---|
| TEGIN ® 4100 (Glyceryl Stearate) | 2.0 | 2.0 | 2.0 | 2.0 | 2.0 | 2.0 | 2.0 | 2.0 | 2.0 |
| TEGO ® Alkanol 1618 (Cetearyl Alcohol) | 3.0 | 3.0 | 3.0 | 3.0 | 3.0 | 3.0 | 3.0 | 3.0 | 3.0 |
| Stearic Acid | 1.0 | 1.0 | 1.0 | 1.0 | 1.0 | 1.0 | 1.0 | 1.0 | 1.0 |
| TEGOSOFT ® AC (Isoamyl Cocoate) | 2.0 | 2.0 | 2.0 | 2.0 | 2.0 | 2.0 | 2.0 | 2.0 | 2.0 |
| TEGOSOFT ® M (Isopropyl Myristate) | 4.5 | 4.5 | 4.5 | 4.5 | 4.5 | 4.5 | 4.5 | 4.5 | 4.5 |
| TEGOSOFT ® CT (Caprylic/Capric Triglyceride) | 7.3 | 7.3 | 7.3 | 7.3 | 7.3 | 7.3 | 7.3 | 7.3 | 7.3 |
| TEGO ® Care CG 90 (Cetearyl Glucoside) | 1.0 | 1.0 | 1.0 | 1.0 | 1.0 | 1.0 | 1.0 | 1.0 | 1.0 |
| TEGO ® Carbomer 134 (Carbomer) | 0.2 | 0.2 | 0.2 | 0.2 | 0.2 | 0.2 | 0.2 | 0.2 | 0.2 |
| Glycerin | 3.0 | 3.0 | 3.0 | 3.0 | 3.0 | 3.0 | 3.0 | 3.0 | 3.0 |
| Sodium Hydroxide (10%) | 0.4 | 0.4 | 0.4 | 0.4 | 0.4 | 0.4 | 0.4 | 0.4 | 0.4 |
| Sphinganine | 0.2 | 0.2 | 0.2 | 0.2 | 0.2 | 0.2 | 0.2 | 0.2 | 0.2 |
| Creatine | 1.0 | | | | | | | | |
| Caffeine | | 1.0 | | | | | | | |
| Carnitine | | | 0.5 | | | | | | |
| Biotin | | | | 0.5 | | | | | |
| Arjunolic acid | | | | | 0.2 | | | | |
| Xymenynic acid | | | | | | 0.2 | | | |
| Minoxidil | | | | | | | 1.0 | | |
| Arginine | | | | | | | | 1.0 | |
| Creatinine | | | | | | | | | 1.0 |
| Water | 74.4 | 74.4 | 74.9 | 74.9 | 75.1 | 75.1 | 74.4 | 74.4 | 74.4 |

Each formulation was assessed by the same panel consisting of 20 trained experts. Specifically, in each case 30 mg of the cream were applied to areas cleaned beforehand with ethanol and marked by means of a stamp (area 7 cm²) on the inside of the forearms. Application was carried out according to a standardized pattern, i.e. each panel participant firstly spread the respective cream pattern on the test field using circular motions with the index finger until absorption of the test sample. After the first 5 circles the spreadability was evaluated, and when spreading was complete absorption, oiliness, waxiness, slippiness, stickiness and silkiness/velvetiness were evaluated. The panel participants then awarded numerical values which describe the sensory properties of the respective cream formulation. The meaning of the assigned points is explained in FIG. 2. Table 2 shows the average points awarded (n=20) for the creams with the named active ingredients.

TABLE 2

Sensory properties of cream formulations comprising various cosmetic active ingredient combinations

| | A | B | C | D | E | F | G | H | I | J | K |
|---|---|---|---|---|---|---|---|---|---|---|---|
| Spreadability | 4 | 4 | 3 | 5 | 3 | 3 | 4 | 4 | 4 | 5 | 4 |
| Absorption | 5 | 6 | 5 | 5 | 6 | 4 | 6 | 5 | 5 | 4 | 5 |
| Oiliness | 6 | 5 | 5 | 6 | 5 | 5 | 7 | 5 | 5 | 6 | 6 |

TABLE 2-continued

Sensory properties of cream formulations comprising various cosmetic active ingredient combinations

| | | | | | | | | | | |
|---|---|---|---|---|---|---|---|---|---|---|
| Waxiness | 5 | 4 | 6 | 6 | 5 | 4 | 6 | 4 | 6 | 4 | 5 |
| Slippiness | 4 | 4 | 4 | 3 | 5 | 5 | 3 | 4 | 5 | 4 | 3 |
| Stickiness | 7 | 6 | 7 | 6 | 7 | 7 | 6 | 8 | 6 | 7 | 7 |
| Silkiness/velvetiness | 3 | 3 | 4 | 2 | 3 | 4 | 2 | 3 | 3 | 3 | 3 |

| | B + C | B + D | B + E | B + F | B + G | B + H | B + I | B + J | B + K |
|---|---|---|---|---|---|---|---|---|---|
| Spreadability | 5 | 3 | 5 | 7 | 3 | 5 | 6 | 5 | 4 |
| Absorption | 7 | 5 | 4 | 6 | 5 | 5 | 4 | 5 | 7 |
| Oiliness | 6 | 7 | 6 | 5 | 6 | 3 | 5 | 6 | 6 |
| Waxiness | 4 | 6 | 3 | 5 | 6 | 4 | 4 | 4 | 5 |
| Slippiness | 3 | 5 | 5 | 4 | 7 | 4 | 5 | 4 | 4 |
| Stickiness | 4 | 3 | 3 | 4 | 4 | 5 | 4 | 5 | 3 |
| Silkiness/velvetiness | 3 | 5 | 3 | 2 | 4 | 3 | 3 | 5 | 4 |

A, vehicle; B, sphinganine; C, creatine; D, caffeine; E, carnitine; F, biotin; G, arjunolic acid; H, xymenynic acid; I, minoxidil; J, arginine; K, creatinine; meaning of the numerical values: see FIG. 2. Indicated values represent the average of 20 panellists.

Surprisingly, the pairwise combination of sphinganine with the cosmetic active ingredients listed in Table 1 led to a considerably improved sensory profile as regards skin feel. This was most marked in the case of stickiness. The cream with sphinganine as the sole active ingredient exhibited here only a slight improvement in the stickiness parameter (6 points compared to the vehicle control with 7 points). By contrast, in the pairwise combination with the named active ingredients, values between 3 and 5 were achieved for the stickiness on average, i.e. the stickiness was in each case significantly reduced compared to the vehicle. Positive effects on the skin feel were moreover also evident for the following active ingredient combinations (in each case compared to the vehicle):

sphinganine and biotin, and also sphinganine and minoxidil improved the spreadability of the cream on the skin (7 and 6 compared with 4 points)

sphinganine and creatine, and also sphinganine and creatinine increased the absorption, and therefore the incorporation of the cream into the skin (in each case 7 compared with 5 points)

sphinganine and xymenynic acid reduced the oiliness of the cream on the skin (3 compared to 6 points)

sphinganine and carnitine reduced the waxiness of the cream on the skin (3 compared to 5 points)

sphinganine and arjunolic acid improved the slippiness of the cream on the skin (7 compared to 4 points)

sphinganine and caffeine, and also sphinganine and arginine improved the silkiness of the cream on the skin (in each case 5 compared to 3 points)

The cosmetic formulations comprising sphinganine in combinations with in each case one of the above-listed active ingredients thus surprisingly exhibited in application tests an improved sensory profile compared to formulations which comprise only sphinganine or one of the other individual active ingredients.

The invention claimed is:

1. A formulation, comprising:
   component A): sphinganine in an amount of at least 0.05% by weight; and
   component B): one or more active ingredients selected from the group consisting of: creatine; creatinine; caffeine; carnitine; biotin; arjunolic acid; xymenynic acid; minoxidil; arginine; and derivatives thereof, wherein said derivatives are acids, esters, amides, alcohols, alcoholates, aldehydes, amines, salts, hydrates, glucosides, isomers or enantiomers of said active ingredients;
   and wherein sphinganine and said active ingredients are present in amounts such that said formulation is more effective at stimulating the proliferation of follicular dermal papilla cells in vitro, or hair growth in vivo, than the stimulation that can be obtained when either said sphinganine or said active ingredients are present in the absence of the other.

2. The formulation of claim 1, wherein component B comprises one or more derivatives selected from the group consisting of: creatine hydrates; disodium phosphocreatine; caffeine benzide; caffeine carboxylic acid; caffeine hydrates; carnitine HCl; acetyl carnitine; acetyl carnitine HCl; carnitine fumarate; carnitine hydroxycitrate; carnitine linoleate; carnitine pyroglutamate; carnitine tartrate; palmitoyl carnitine; D/L-carnitine; D/L-carnitine HCl; hexadecanoyl carnitine; levo carnitine; allantoin biotin; biotinoyl hexapeptide-2 amide; biotinoyl pentapeptide-4; biotinoyl tripeptide-1; biotinoyl tripeptide-35; ethyl biotinate; monoethanolamine biotinate biotin ethyl ester; biotinum; acetyl arginine; and arginine HCl.

3. The formulation of claim 1, wherein component A is present at a concentration of 0.05% by weight to 5.0% by weight.

4. The formulation of claim 1, wherein component B is present at a concentration of 0.01% by weight to 20.0% by weight.

5. The formulation of claim 2, wherein component B is present at a concentration of 0.01% by weight to 20.0% by weight.

6. The formulation of claim 3, wherein component B is present at a concentration of 0.01% by weight to 20.0% by weight.

7. The formulation of claim 2, wherein component A is present at a concentration of 0.05% by weight to 1.0% by weight.

8. The formulation of claim 7, wherein component B is present at a concentration of 0.01% by weight to 20.0% by weight.

9. The formulation of claim 1, wherein the weight ratio of component A to component B is 1:1 to 1:2000.

10. The formulation of claim 9, wherein component B comprises one or more derivatives selected from the group consisting of: creatine hydrates; disodium phosphocreatine; caffeine benzide; caffeine carboxylic acid; caffeine hydrates; carnitine HCl; acetyl carnitine; acetyl carnitine HCl; carnitine fumarate; carnitine hydroxycitrate; carnitine linoleate; carnitine pyroglutamate; carnitine tartrate; palmitoyl carnitine; D/L-carnitine; D/L-carnitine HCl; hexadecanoyl carnitine; levo carnitine; allantoin biotin; biotinoyl hexapeptide-2 amide; biotinoyl pentapeptide-4; biotinoyl tripeptide-1; biotinoyl tripeptide-35; ethyl biotinate; monoethanolamine biotinate biotin ethyl ester; biotinum; acetyl arginine; and arginine HCl.

11. The formulation of claim 9, wherein component A is present at a concentration of 0.05% by weight to 5.0% by weight.

12. The formulation of claim 9, wherein component B is present at a concentration of 0.01% by weight to 20.0% by weight.

13. The formulation of claim 10, wherein component B is present at a concentration of 0.01% by weight to 20.0% by weight.

14. The formulation of claim 11, wherein component B is present at a concentration of 0.01% by weight to 20.0% by weight.

15. The formulation of claim 10, wherein component A is present at a concentration of 0.05% by weight to 1.0% by weight.

16. The formulation of claim 15, wherein component B is present at a concentration of 0.01% by weight to 20.0% by weight.

\* \* \* \* \*